United States Patent [19]

Kalfa et al.

[11] 4,335,615

[45] Jun. 22, 1982

[54] EQUIPMENT FOR TESTING MATERIALS FOR STRESS CORROSION CRACKING

[75] Inventors: Horst Kalfa, Frankfurt; Bruno Schubert, Langen; Peter Brunmayer, Usingen; Siegfried Gellermann, Mainz, all of Fed. Rep. of Germany

[73] Assignee: DECHEMA, Fed. Rep. of Germany

[21] Appl. No.: 154,983

[22] Filed: May 30, 1980

[30] Foreign Application Priority Data

Jun. 15, 1979 [DE] Fed. Rep. of Germany ... 7917161[U]

[51] Int. Cl.³ .......................................... G01N 19/08
[52] U.S. Cl. ........................................ 73/799; 73/826
[58] Field of Search ........................ 73/799, 830, 826

[56] References Cited

U.S. PATENT DOCUMENTS

| | | | |
|---|---|---|---|
| 1,485,835 | 4/1924 | Bothezat et al. | 73/826 |
| 1,499,546 | 7/1924 | Oxley | 73/830 |
| 1,877,467 | 9/1932 | Lake | 73/826 |
| 2,185,340 | 1/1940 | Howe | 73/826 |
| 4,030,348 | 6/1977 | Fletcher et al. | 73/826 |

Primary Examiner—Anthony V. Ciarlante

Attorney, Agent, or Firm—Armstrong, Nikaido, Marmelstein & Kubovcik

[57] ABSTRACT

Equipment for testing materials for the effects of stress corrosion cracking, which includes more than two tensioning units, each consisting of a base plate, two guide bars, an upper and a lower cross-beam, a locking system for the guide of the lower cross-beam and a connecting flange between the cross-beam and a threaded bar for causing elongation of a test sample. The power drive supply block drives the threaded bar. A motor power unit is included in the power drive supply block and vertically-slippable gearing is inserted between the motor gearing and the block. The motor power unit consists of two stepping motors driving sun gears. The sun gears drive planetary gears which, by means of an arm, drive the drive shaft operatively associated with the threaded bar. In particular, the invention relates to equipment with six tensioning units comprising an automatic limit switch-off means and a lift system in the power drive supply block for separating the drive gears from the rest of the system. The angular speed of the stepping motors can be controlled by an electrically generated stepping frequency, the control unit, if desired, consisting of a microprocessor and a memory.

7 Claims, 7 Drawing Figures

STEPPING MOTORS

EQUIPMENT FOR TESTING MATERIALS FOR STRESS CORROSION CRACKING

The present invention relates to an apparatus for testing metal, more specifically, an apparatus for measuring the effects of stress corrosion cracking on a piece of metal.

Previously material testing for stress corrosion cracking was implemented on so-called Constant-Strain-Rate (CSR) equipment, which loads a sample at a constant strain rate until rupture. Cyclical loading has also been used. The sample is mounted in a sample holding means and loaded by downward motion of a lower cross-beam. The upper end of the sample holding means is mounted in an upper stationary cross-beam. A middle cross-beam is used to guide the lower moving cross-beam. The motions of the lower cross-beam can be effected in CSR equipment by the gearing and the motor present and are proportional to the elongation of the sample.

The operation of the equipment is determined purely by its structural features, but does not take into account the needs of the practical users. The areas of art in which the CSR equipment is used can be characterized by the fields of:

(a) materials development;
(b) testing the materials' applications; and
(c) quality control.

The requirements set therein are not, or are at least only imperfectly, met by the prior art CSR equipment.

It is necessary, particularly in materials development and testing of applicability, that the material be tested under conditions closely approximating those of ultimate usage. Loads applied to aggregates must be reproducibly simulated in the lab.

This requires that the movable cross-beam of a CSR equipment be moved by means of motor and gearing following the load functions occurring in actual usage. That is, the cross-beam must carry out a continuously adjustable up-and-down motion. This requires that motor and gearing deliver continuously adjustable angular speeds in the positive and negative direction of rotation. This is impossible for the designs of the known art.

When testing the applicability of the materials, it is important that the designer know the characteristics of various materials to determine the use of the proper material for a specific function. To ascertain these characteristics, the mechanics of fracture are used. Tension tests are carried out on tension samples or so-called constant tension (CT) samples until fracture. The growth in cracks at constant load is monitored. To that end, a sample under load must be relieved in load in relation to the measured increase in cracks. The equipment, therefore, is required to convert an electronic signal of growth of cracks into a proportional load relief. This is impossible with the known equipment.

Quality control of materials involves comprehensive routine testing. The testing times are relatively long, typically three days, and require much machinery. Thus, there is an economic requirement for several tensioning units per machine. Such equipment so far is non-existent.

The above drawbacks are eliminated by a CSR equipment of the present invention which comprises several tensioning units per single apparatus, for which the angular speed of the drive unit can be continuously controlled in the positive and negative sense of rotation and where the control of angular speed can be implemented by an electronic signal.

The CSR equipment of the invention consists of four main elements, namely:

(1) the tensioning units;
(2) the drive supply block;
(3) vertically-slippable gear system;
(4) the motor power unit;

which are described in detail below in relation to the drawings.

DETAILED DESCRIPTION OF THE PREFERRED EMBODIMENTS

Figure 1:
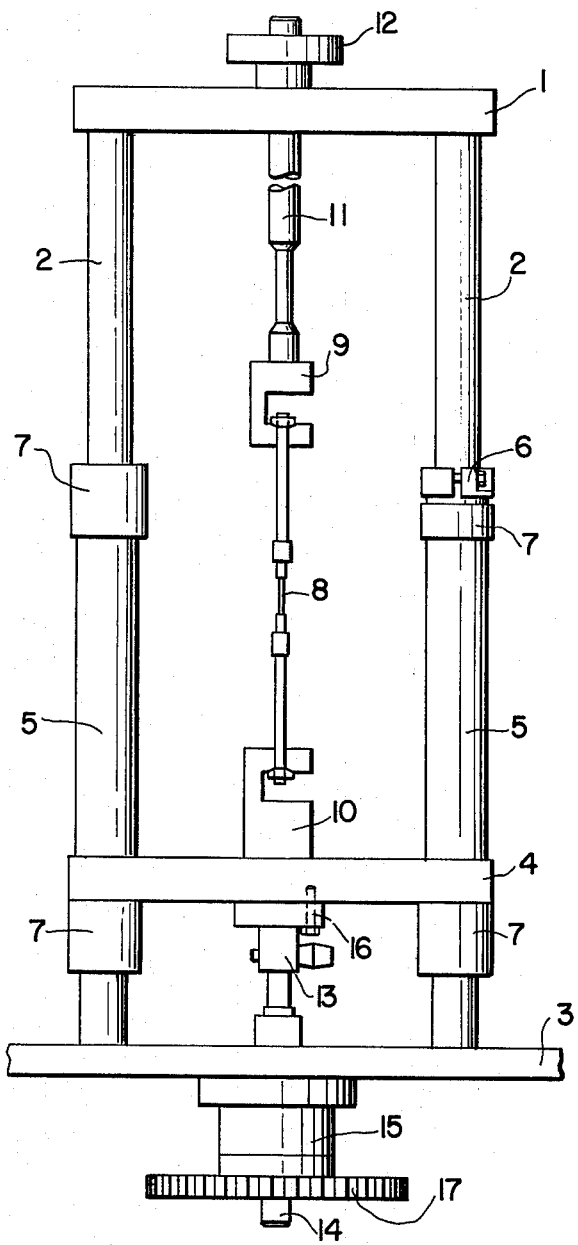
FIG. 1 shows an elevation of a basic tensioning unit of the present invention.

The tension unit shown in FIG. 1 includes a frame made up of an upper cross-beam (1), two guide posts (2) and a base plate (3). A movable lower cross-beam (4) is guided by a tubular guide (5) in this frame. The tubular guide (5) can be locked in place by a clamping system (6) consisting of a slotted guide nut (7) when a sample (8) is installed or removed. The sample (8) is hooked into upper and lower quick-disconnect heads (9) and (1) of an upper sample holding means (11) and the cross-beam (4), respectively. The upper sample holding means (11) consists of a threaded rod which is supported in the upper cross-beam (1) in height-adjustable manner by a cylindrical nut (12). The lower cross-beam (4) is loaded when the sample is lowered, and is connected by means of a flange (13) with a second threaded rod (14) and a pin with a traction nut (15). The path of the force can be interrupted at flange (13) when tension is being applied by loosening three screws (16). This allows removal of the sample (8) before it fractures. The drive of the traction nut (15) is implemented by a gear power block through the gear (17).

The number of tensioning units exceeds 2 and is limited upward only for the reasons of bulk and operational reasons. Therefore, equipment with 6 or 8 tensioning units is preferred.

Figure 2A:
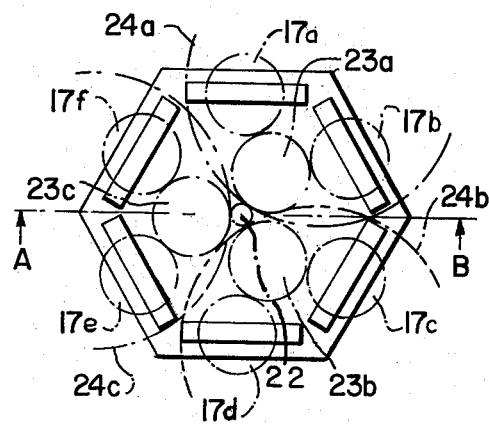
FIG. 2A shows a plan diagrammatic view of a plurality of tensioning units mounted together in accordance with the present invention.
Figure 2B:
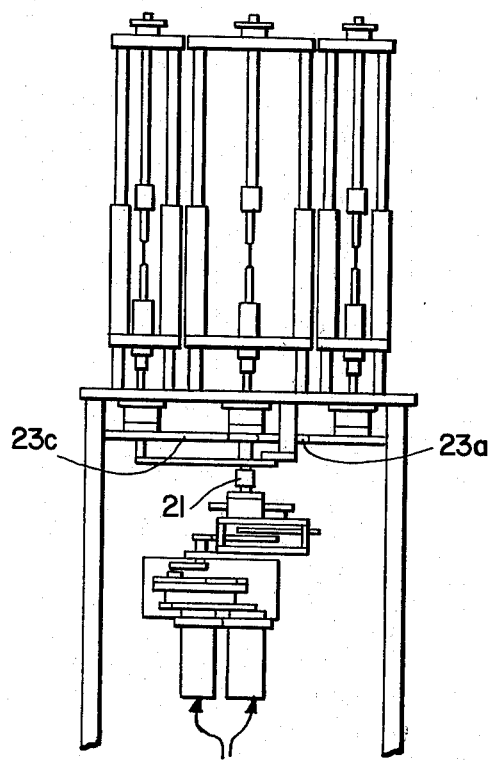
FIG. 2B shows a sectional view along lines A-B of FIG. 2A.
Figure 3:
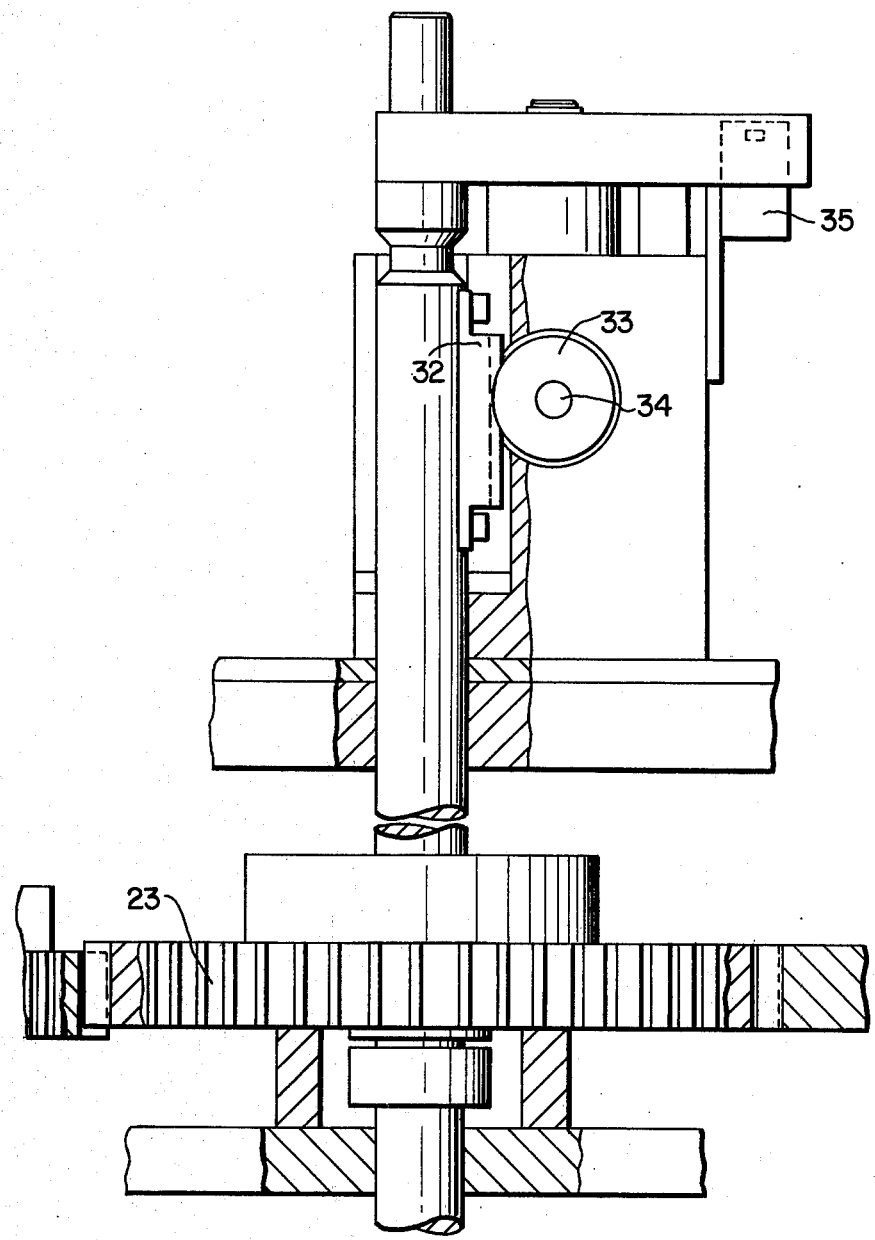
FIG. 3 shows a detailed view, partly in cross-section, of a left system to remove certain drive gears from the power train in a multiple unit device as in FIGS. 2A and 2B.

The drive power block is shown in FIGS. 2A and 2B, and consists of a combination of gears arranged as follows, beginning with the drive shaft of the plug-in gearing: The drive shaft (21), together with gear (22), transmits the power to the drive gears (23). The size and the number of the drive gears (23) determine the number of tensioning units. The drive gears (23) may be conventional fixed gearing, and thereby contribute to a fixed staggering of the speeds of the drive units (24). The drive unit (24) consists of one drive gear and 2 driven gears (17a,b) for the traction nuts (15). Alternatively, as shown in FIG. 3, the drive gears (23) may be vertically-slippable, and thus removable, from the power train, by a lift system whereby the remaining drive gears (23) can run continuously. A gear rack (32) is mounted on the extended shaft of the drive gear, with the rack being meshed by a gear driven from a motor shaft (34) by a lift motor (not shown). The lift motor can be controlled by a limit switch (54), a limit switch (35) and a pressure switch (not shown).

The vertically-slippable gearing (23) consists of a combination of several gears corresponding to an ordinary fixed gearing. It is used to reduce the angular speed and to increase the traction torque of the motor power unit.

Figure 4:
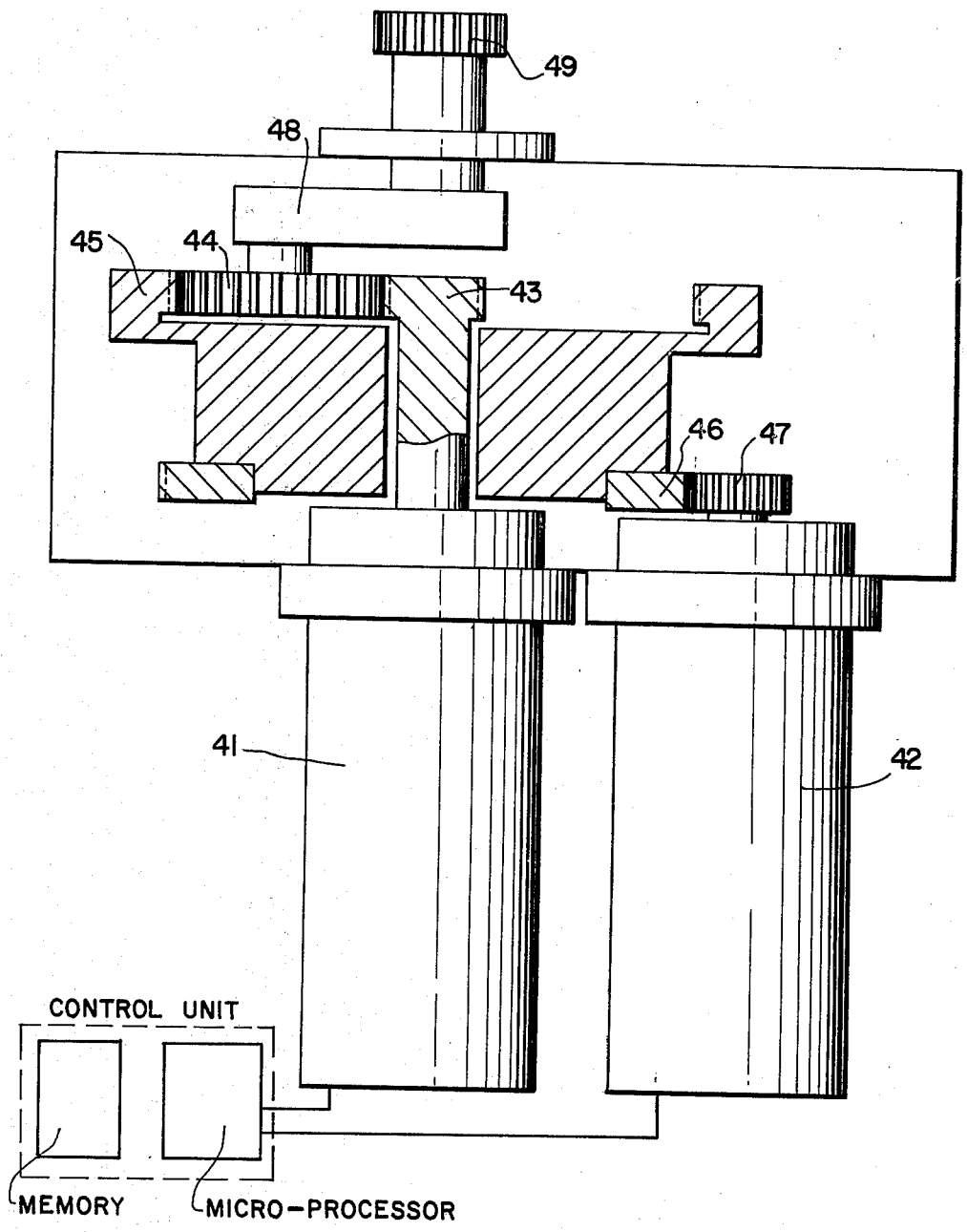
FIG. 4 shows, in partial cross-section, a motor power unit of the present invention.

FIG. 4 shows the motor power unit which operates on the principle of the bilaterally driven planetary gearing. A first stepping motor (41) rotates to an angular speed kept constant electronically and exerts a torque by gear (43) on gear crown (45). The gear (44) therefore rotates with the gear crown (45). If a second stepping motor (42), by means of the gear crowns (45) and (46) drives gear (47) where the second stepping motor (42) runs in the same sense of rotation and at the same angular speed as the first stepping motor (41), then the axis of gear (44) remains stationary and only will rotate about an arm (48) while the arm (48) remains in place. This presumes the same number of teeth for both gears (44) and (47) and for the gear crowns (45) and (46). If the angular speed of one motor is slightly varied, the gear (44) will move within the gear crown (45) and cause a rotation of the drive shaft (49). Depending on the sign of the difference in angular speed between motors (41) and (42), the sense of rotation will vary. The magnitude of the difference in angular speed determines the angular speed of the drive shaft (49). Drive shaft (49) is interconnected through conventional gear to drive shaft (21) of FIGS. 2A and B. The angular speed of the stepping motors (41) and (42) can be predetermined and controlled by an electronically generated stepping frequency means or a control unit consisting of an appropriately programmed microprocessor and memory.

Figure 5:
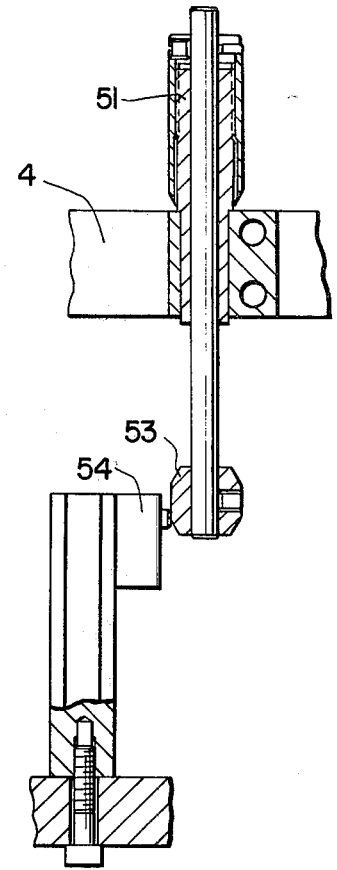
FIG. 5 shows a sectional detail along lines A-B of FIG. 6.
Figure 6:
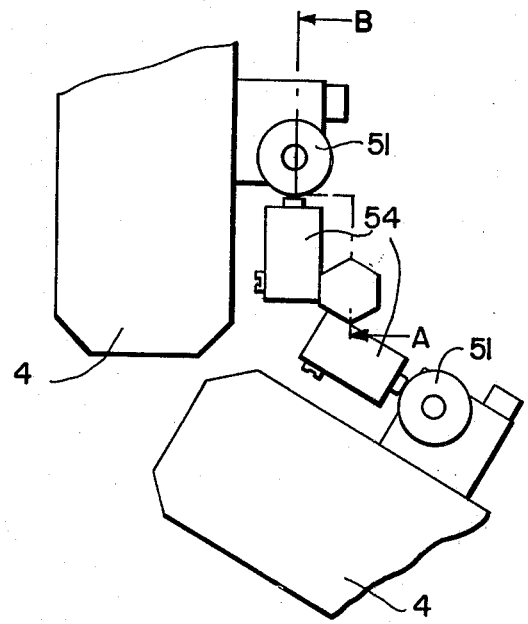
FIG. 6 shows a plan of a mounting arrangement for an automatic limit switch-off means of the present invention.

FIGS. 5 and 6 show an automatic limit switch-off means for controlling a tensioning unit. It includes a micrometer (51) mounted on a lower cross-beam (4) carrying a switch body (53), adjustable in position, which interacts with and actuates a limit switch 54.

What is claimed:

1. Apparatus for testing materials for stress corrosion cracking comprising:
    (a) at least two tensioning units, each unit including a base plate (3), two guide columns (2) mounted on said plate, an upper stationary cross-beam (1) mounted on said columns, a lower movable cross-beam (4) vertically slidable on said columns, means for clamping said lower cross-beam to said columns, sample holding means, and means for moving said lower cross-beam, said lower cross-beam comprising a cross plate, four guide nuts (7) and two tubes (5), said guide nuts being mounted on the ends of the tubes which ride on said columns and carry said cross-plate, said clamping means comprising a slotted guide nut (6) operatively associated and carried by one of said tubes, said holding means comprising quick coupling means (9),(10) connected with said upper and lower cross-beams, said cross plate carrying a connecting flange 13 secured to said cross-plate by detachable screws; and
    (b) a drive power block mounted on said base plate comprising at least one drive gear (23) operatively associated with said means for moving said lower cross-beam and a motor power unit driving said at least one drive gear, said motor power unit comprising two stepping motors (41,42), a sun gear (43) driven by one stepping motor, an annular crown gear (45) driven by the other stepping motor, at least one planetary gear (44) in driving engagement with said gun gear and said crown gear, an arm (48) carrying said planetary gear and a drive shaft (49) carrying said arm, said drive shaft being operatively associated with said at least one drive gear.

2. Apparatus according to claim 1 comprising six hexagonally arranged tensioning units.

3. Apparatus according to claim 1 wherein each of said tensioning units additionally comprises an automatic limit switch-off means comprising a micrometer (51) mounted to said lower cross-beam (4) and a switch-body (53) adjustable in height and mounted to the lower end of said micrometer, which actuates a limit switch (54).

4. Apparatus according to claim 2 wherein each of said tensioning units additionally comprises an automatic limit switch-off means comprising a micrometer (51) mounted to said lower cross-beam (4) and a switch-body (53) adjustable in height and mounted to the lower end of said micrometer, which actuates a limit switch (54).

5. Apparatus according to any one of claims 1, 2, 3 or 4 wherein said drive power block further comprises a lift means for at least one drive gear for separating the drive gear from the means for moving, said lift means comprising gear-rack (32) on an extended shaft of the at least one drive gear and a gear (33) engaging a motor shaft (34) of a lift motor mounted on said base plate (3), said at least one drive gear being vertically slippable.

6. Apparatus according to claim 1 wherein the angular speed of the stepping motors is controlled by an electronically generated stepping frequency.

7. Apparatus according to claim 6 wherein the angular speed control for operating a constant or time-varying angular speed is achieved using a control unit consisting of a microprocessor and a memory.

* * * * *